United States Patent
Ziv et al.

(10) Patent No.: US 11,331,213 B2
(45) Date of Patent: May 17, 2022

(54) DEVICES AND METHODS FOR PELVIC ORGAN PROLAPSE ALLEVIATION

(71) Applicant: ConTIPI Medical Ltd., Caesarea (IL)

(72) Inventors: Elan Ziv, Ramat-Gan (IL); Zohar Tyroler, Hod-HaSharon (IL); Elisheva Fabrikant, Herzlia (IL); Tal Caspi, Pardes Chana-Karkur (IL)

(73) Assignee: ConTIPI Medical Ltd., Caesarea (IL)

( * ) Notice: Subject to any disclaimer, the term of this patent is extended or adjusted under 35 U.S.C. 154(b) by 555 days.

(21) Appl. No.: 15/767,390

(22) PCT Filed: Oct. 13, 2016

(86) PCT No.: PCT/IL2016/051114
§ 371 (c)(1),
(2) Date: Apr. 11, 2018

(87) PCT Pub. No.: WO2017/064714
PCT Pub. Date: Apr. 20, 2017

(65) Prior Publication Data
US 2018/0296387 A1 Oct. 18, 2018

Related U.S. Application Data

(63) Continuation-in-part of application No. 14/881,200, filed on Oct. 13, 2015.
(Continued)

(51) Int. Cl.
*A61F 6/12* (2006.01)
*A61F 6/08* (2006.01)

(52) U.S. Cl.
CPC . *A61F 6/12* (2013.01); *A61F 6/08* (2013.01)

(58) Field of Classification Search
USPC ........ 128/834, 838–840, 836, 837, 833–840; 600/29; 604/14, 515
See application file for complete search history.

(56) References Cited

U.S. PATENT DOCUMENTS

| 7,050 A | 1/1850 | Caulkins et al. |
|---|---|---|
| 80,163 A | 7/1868 | Gorgas et al. |

(Continued)

FOREIGN PATENT DOCUMENTS

| CN | 2464263 | 12/2001 |
|---|---|---|
| CN | 101287422 | 10/2008 |

(Continued)

OTHER PUBLICATIONS

Dictionary.com definition of 'circumference' (Year: 2021).*
(Continued)

*Primary Examiner* — Keri J Nelson
*Assistant Examiner* — Trisha Talapatra (57) ABSTRACT

A device sized and shaped for alleviating organ prolapse when inserted into a vagina, comprising: (a) an adjustably flexible, substantially planar ring provided with at least one opposing snapping element; (b) a central rod extending at least partially through the ring transverse to the snapping elements, where the central rod is provided with counterpart slots configured for insertion of the snapping elements therein; and, (c) a connection block, co-axial with the central rod and slidable thereover to transition the device from an expanded state to a collapsed state, configured with slots which align with the counterpart slots of the central rod for passage of at least one snapping element therethrough when the device is in the collapsed state.

11 Claims, 4 Drawing Sheets

Related U.S. Application Data (60) Provisional application No. 62/240,552, filed on Oct. 13, 2015.

(56) References Cited

U.S. PATENT DOCUMENTS

| | | | |
|---|---|---|---|
| 1,334,237 | A | 3/1920 | Fleck |
| 2,201,274 | A | 5/1940 | Singer |
| 2,398,518 | A | 5/1946 | Clark |
| 3,811,423 | A | 5/1974 | Dickinson, III et al. |
| 4,246,896 | A | 1/1981 | Horne, Jr. et al. |
| 4,307,716 | A | 12/1981 | Davis |
| 4,620,534 | A | 11/1986 | Zartman |
| 4,677,967 | A | 7/1987 | Zartman |
| 4,823,814 | A | 4/1989 | Drogendijk et al. |
| 5,014,722 | A * | 5/1991 | Bauer ............ A61F 6/142 128/830 |
| 5,224,494 | A | 7/1993 | Enhorning |
| 5,355,896 | A * | 10/1994 | Schulman .......... A61F 6/08 128/834 |
| 5,632,756 | A | 5/1997 | Kruglick |
| 5,771,899 | A | 6/1998 | Martelly et al. |
| 5,894,842 | A | 4/1999 | Rabin et al. |
| 6,158,435 | A * | 12/2000 | Dorsey ............ A61F 2/005 128/830 |
| 6,216,698 | B1 | 4/2001 | Regula |
| 6,503,190 | B1 | 1/2003 | Ulmsten et al. |
| 6,645,137 | B2 | 11/2003 | Ulmsten et al. |
| 6,808,485 | B2 | 10/2004 | Zunker |
| 6,982,515 | B2 | 1/2006 | Howell et al. |
| 7,036,511 | B2 | 5/2006 | Nissenkorn |
| 8,302,608 | B2 | 11/2012 | Harmani |
| 8,573,221 | B2 | 11/2013 | Sakhel |
| 8,651,109 | B2 | 2/2014 | Ziv et al. |
| 8,728,013 | B2 | 5/2014 | Perle et al. |
| 10,507,094 | B2 | 12/2019 | Harmanli |
| 2003/0149334 | A1 | 8/2003 | Ulmsten et al. |
| 2008/0009931 | A1 | 1/2008 | Bartning et al. |
| 2008/0167599 | A1 | 7/2008 | Osborn et al. |
| 2008/0281149 | A1 * | 11/2008 | Sinai ............ A61F 2/005 600/32 |
| 2009/0171139 | A1 | 7/2009 | Chu |
| 2009/0203959 | A1 | 8/2009 | Ziv et al. |
| 2009/0266367 | A1 * | 10/2009 | Ziv ............ A61F 2/005 128/834 |
| 2009/0283099 | A1 * | 11/2009 | Harmanli ............ A61F 2/005 128/834 |
| 2010/0286791 | A1 | 11/2010 | Goldsmith |
| 2013/0025604 | A1 | 1/2013 | Harmanli |
| 2013/0053863 | A1 | 2/2013 | Juravic et al. |
| 2013/0324381 | A1 | 12/2013 | Horsley |
| 2013/0327338 | A1 | 12/2013 | Churchill et al. |
| 2014/0073846 | A1 | 3/2014 | Sinai et al. |
| 2014/0100416 | A1 | 4/2014 | Purling et al. |
| 2014/0158138 | A1 | 6/2014 | Ziv et al. |
| 2014/0261445 | A1 | 9/2014 | Maaskamp et al. |
| 2014/0275744 | A1 | 9/2014 | Rosen et al. |
| 2015/0133725 | A1 | 5/2015 | Ziv et al. |
| 2016/0015500 | A1 | 1/2016 | Ziv et al. |
| 2017/0100278 | A1 | 4/2017 | Ziv et al. |
| 2018/0296388 | A1 | 10/2018 | Ziv et al. |

FOREIGN PATENT DOCUMENTS

| | | |
|---|---|---|
| CN | 101511302 | 8/2009 |
| CN | 102083389 | 6/2011 |
| CN | 202313882 | 7/2012 |
| CN | 102753124 | 10/2012 |
| DE | 169862 | 7/1905 |
| EP | 2276419 | 11/2011 |
| FR | 2843700 | 2/2004 |
| GB | 235218 | 10/1925 |
| GB | 1115727 | 5/1968 |
| JP | 06-133996 | 5/1994 |
| WO | WO 96/01084 | 1/1996 |
| WO | WO 03/047476 | 6/2003 |
| WO | WO 2004/103213 | 12/2004 |
| WO | WO 2008/079271 | 7/2008 |
| WO | WO 2009/130702 | 10/2009 |
| WO | WO 2014/127270 | 8/2014 |
| WO | WO 2014/127295 | 8/2014 |
| WO | WO 2017/064712 | 4/2017 |
| WO | WO 2017/064713 | 4/2017 |
| WO | WO 2017/064714 | 4/2017 |

OTHER PUBLICATIONS

Official Action dated Jul. 16, 2019 From the US Patent and Trademark Office Re. U.S. Appl. No. 14/881,200. (28 pages).
Supplementary European Search Report and the European Search Opinion dated Jun. 24, 2019 From the European Patent Office Re. Application No. 16855065.5. (8 Pages).
Supplementary European Search Report and the European Search Opinion dated Jun. 24, 2019 From the European Patent Office Re. Application No. 16855064.8. (9 Pages).
Supplementary Partial European Search Report and the European Search Opinion dated Sep. 9, 2019 From the European Patent Office Re. Application No. 16855066.3. (10 Pages).
Official Action dated Dec. 2, 2019 From the US Patent and Trademark Office Re. U.S. Appl. No. 14/881,200. (17 pages).
Notification of Office Action and Search Report dated Oct. 24, 2019 From the State Intellectual Property Office of the People's Republic of China Re. Application No. 201680072943.2. (9 Pages).
Translation of Notification dated Nov. 17, 2019 From OA of People's Republic of China Re. Application No. 201680072943.2. (9 Pages).
Notification of Office Action and Search Report dated Dec. 18, 2019 From the State Intellectual Property Office of the People's Republic of China Re. Application No. 201680072759.8 and Its Translation of Office Action Into English. (6 Pages).
International Preliminary Report on Patentability dated Apr. 26, 2018 From the International Bureau of WIPO Re. Application No. PCT/IL2016/051112. (9 Pages).
International Preliminary Report on Patentability dated Apr. 26, 2018 From the International Bureau of WIPO Re. Application No. PCT/IL2016/051113. (8 Pages).
International Preliminary Report on Patentability dated Apr. 26, 2018 From the International Bureau of WIPO Re. Application No. PCT/IL2016/051114. (8 Pages).
International Search Report and the Written Opinion dated Mar. 2, 2017 From the International Searching Authority Re. Application No. PCT/IL2016/051114. (12 Pages).
International Search Report and the Written Opinion dated Mar. 3, 2017 From the International Searching Authority Re. Application No. PCT/IL2016/051113. (13 Pages).
International Search Report and the Written Opinion dated Apr. 20, 2017 From the International Searching Authority Re. Application No. PCT/IL2016/051112. (15 Pages).
Invitation to Pay Additional Fees Dated Feb. 2, 2017 From the International Searching Authority Re. Application No. PCT/IL2016/051112. (2 Pages).
Advisory Action dated Apr. 9, 2020 From the US Patent and Trademark Office Re. U.S. Appl. No. 14/881,200. (4 Pages).
Notification of Office Action and Search Report dated Jun. 11, 2020 From the State Intellectual Property Office of the People's Republic of China Re. Application No. 201680072760.0. (8 Pages).
Notification of Office Action and Search Report dated Apr. 16, 2020 From the State Intellectual Property Office of the People's Republic of China Re. Application No. 201680072759.8. (7 Pages).
Notification of Office Action Dated Apr. 20, 2020 From the State Intellectual Property Office of the People's Republic of China Re. Application No. 201680072943.2. (4 Pages).
Official Action dated May 13, 2020 from the US Patent and Trademark Office Re. U.S. Appl. No. 14/881,200. (13 pages).
Search Report and Explanationd dated Jun. 9, 2020 From the Servico Publico Federal, Ministerio da Economia, Institute National da Propriedade Industrial do Brasil Re. BR112018007546-9 and Its Summary in English. (5 Pages).

(56) References Cited

OTHER PUBLICATIONS

Search Report and Explanationd dated Jun. 9, 2020 From the Servico Publico Federal, Ministerio da Economia, Institute National da Propriedade Industrial do Brasil Re. BR112018007548-5 and Its Summary in English. (5 Pages).
Search Report and Explanations dated Jun. 9, 2020 From the Servico Publico Federal, Ministerio da Economia, Institute National da Propriedade Industrial do Brasil Re. Application No. BR112018007542-6 and Its Summary in English. (5 Pages).
Summary dated May 12, 2020 of Notification of Office Action dated Apr. 16, 2020 From the State Intellectual Property Office of the People's Republic of China Re. Application No. 201680072759.8. (2 Pages).
Summary dated May 13, 2020 of Notification of Office Action dated Apr. 20, 2020 From the State Intellectual Property Office of the People's Republic of China Re. Application No. 201680072943.2. (2 Pages).
Interview Summary dated Sep. 9, 2020 from the US Patent and Trademark Office Re. U.S. Appl. No. 14/881,200. (3 pages).
Official Action dated Sep. 17, 2020 from the US Patent and Trademark Office Re. U.S. Appl. No. 15/767,401. (33 pages).
Notification of Office Action dated Dec. 25, 2020 From the State Intellectual Property Office of the People's Republic of China Re. Application No. 201680072760.0. and its English Summary (8 Pages).
Communication Pursuant to Article 94(3) EPC dated May 10, 2021 From the European Patent Office Re. Application No. 16855065.5. (5 Pages).
Decision of Rejection dated May 18, 2021 From the State Intellectual Property Office of the People's Republic of China Re. Application No. 201680072760.0. (5 Pages).
Examination Report Under Sections 12 & 13 of the Patents Act, 1970 and the Patents Rules, 2003 dated May 24, 2021 From the Government of India, Intellectual Property India, Patents, Designs, Trade Marks, Geographical Indications, The Patent Office Re. Application No. 201837017313. (5 Pages).
Final Official Action dated May 28, 2021 from the US Patent and Trademark Office Re. U.S. Appl. No. 15/767,401. (20 pages).
Notification of Decision of Rejection dated Mar. 11, 2021 From the State Intellectual Property Office of the People's Republic of China Re. Application No. 201680072943.2. (6 Pages).
Translation Dated Jun. 8, 2021 of Notification of Decision of Rejection dated Mar. 11, 2021 From the State Intellectual Property Office of the People's Republic of China Re. Application No. 201680072943.2. (10 Pages).
Interview Summary dated Nov. 21, 2021 from US Patent and Trademark Office Re. U.S. Appl. No. 14/881,200. (2 pages).
Communication Pursuant to Article 94(3) EPC dated Sep. 15, 2021 From the European Patent Office Re. Application No. 16855065.5. (4 Pages).
Official Action dated Sep. 20, 2021 from the US Patent and Trademark Office Re. U.S. Appl. No. 14/881,200. (24 pages).
English Summary dated Aug. 12, 2021 of Notification of Office Action dated May 18, 2021 From the State Intellectual Property Office of the People's Republic of China Re. Application No. 201680072760.0. (2 Pages).
Examination Report Under Sections 12 & 13 of the Patents Act, 1977 and the Patents Rules, 2003 dated Jun. 5, 2021 From the Government of India, Intellectual Property India, Patents, Designs, Trade Marks, Geographical Indications, The Patent Office Re. Application No. 201837017323. (6 Pages).
Under Sections 12 & 13 of the Patents Act, 1970 and the Patents Rules, 2003 Dated Jun. 5, 2021 From the Government of India, Intellectual Property India, Patents, Designs, Trade Marks, Geographical Indications, The Patent Office Re. Application No. 201837017341. (7 Pages).

\* cited by examiner

DEVICES AND METHODS FOR PELVIC ORGAN PROLAPSE ALLEVIATION

RELATED APPLICATIONS

This application is a National Phase of PCT Patent Application No. PCT/IL2016/051114 having International filing date of Oct. 13, 2016, which claims the benefit of priority under 35 USC § 119(e) of U.S. Provisional Patent Application No. 62/240,552 filed on Oct. 13, 2015.

PCT Patent Application No. PCT/IL2016/051114 is also a Continuation-In-Part (CIP) of U.S. patent application Ser. No. 14/881,200 filed on Oct. 13, 2015.

The contents of the above applications are all incorporated by reference as if fully set forth herein in their entirety.

FIELD AND BACKGROUND OF THE INVENTION

The present invention, in some embodiments thereof, relates to the health care industry and, more particularly, but not exclusively, to devices and methods for treating feminine pelvic organ prolapse.

Pelvic organ prolapse occurs when the network of muscles, ligaments, and tissues that hold the pelvic organs in place is weakened and one or more pelvic organs descend into the vaginal cavity. Pelvic organ prolapse occurs as a result of normal aging, childbirth, pelvic surgery or trauma, and may include one or more of the following conditions:

i) Cystocele, the leading form of pelvic organ prolapse, wherein the bladder drops into the vagina and may be associated with urination problems;

ii) Rectocele, wherein the rectum herniates into the vagina and may result in difficulty and/or pain with defecation;

iii) Enterocele, wherein the small intestine prolapses into the vagina;

iv) Uterine prolapse wherein the uterus drops downward into the vagina and is often associated other organ prolapse; and v) Vaginal vault prolapse, wherein the top portion of the vagina, the apex, loses its natural shape and drops down into the lower vaginal canal, and may occur in women who had a hysterectomy.

To avoid surgical procedures to treat pelvic organ prolapse, a number of non-surgical vaginal devices, pessaries, have been designed to be inserted into the vagina by a surgeon, medical assistant or user.

Background art includes the following patents, the contents of all of which are incorporated by reference as if fully set forth herein:

| | |
|---|---|
| WO 2009/130702: | Pessaries for Prolapse Alleviation; |
| U.S. Pat. No. 8,651,109: | Pessaries for Prolapse Alleviation; |
| WO 9601084: | Inflatable Vaginal Pessary; |
| GB 235218: | Inflatable Pessary; |
| FR 2843700: | Rehabilitation Device for Urinary and Faecal Continence; |
| WO 03047476: | Vaginal Pessary; |
| GB 1115727: | Apparatus Controlling Incontinence in the Female; |
| U.S. Pat. No. 5,224,494: | Vaginal Pessary; |
| U.S. Pat. No. 6,158,435: | Pessary; |
| US 2003149334: | Vaginal Pessary; |
| JP 6133996: | Pessary for Treating Prolapse of Uterus; |
| U.S. Pat. No. 4,823,814: | Pessary; |
| U.S. Pat. No. 5,771,899: | Pessary; |
| U.S. Pat. No. 5,894,842: | Pessary for Treating Vaginal Prolapse; |
| U.S. Pat. No. 6,158,435: | Pessary; |
| U.S. Pat. No. 6,216,698: | Flexible Pessary; |
| U.S. Pat. No. 6,503,190: | Vaginal Pessary; |
| U.S. Pat. No. 6,808,485: | Compressible Resilient Vaginal Incontinence Insert; and |
| U.S. Pat. No. 7,036,511: | Vaginal Pessary. |

SUMMARY OF THE INVENTION

There is provided in accordance with an exemplary embodiment of the invention, a device sized and shaped for alleviating organ prolapse when inserted into a vagina, comprising: (a) an adjustably flexible, substantially planar ring provided with at least one opposing snapping element; (b) a central rod extending at least partially through the ring transverse to the snapping elements, where the central rod is provided with counterpart slots configured for insertion of the snapping elements therein; and, (c) a connection block, co-axial with the central rod and slidable thereover to transition the device from an expanded state to a collapsed state, configured with slots which align with the counterpart slots of the central rod for passage of at least one snapping element therethrough when the device is in the collapsed state.

In an embodiment of the invention, the at least one snapping element snaps to another snapping element both of which pass through the counterpart slots of the central rod and the slots of the connection block.

In an embodiment of the invention, the device further comprises a padded elastic cover around at least a portion of the ring.

In an embodiment of the invention, the device further comprises a removal string configured to detach a distal end of the connection block from the ring upon the application of a proximal force on the removal string.

There is further provided in accordance with an exemplary embodiment of the invention, a device sized and shaped for alleviating organ prolapse when inserted into a vagina, comprising: (a) an adjustably flexible, substantially planar ring provided with a plurality of self-snapping elements; (b) a central rod extending at least partially through the ring transverse to the snapping elements; and, (c) a connection block coaxial with the central rod and configured to be detachable from a distal side of the ring opposite the central rod, where the self-snapping elements are configured to removably attach to each other to configure the device in a collapsed state and where the central rod is slidable to detach the self-snapping elements from each other to return the device to an expanded state.

In an embodiment of the invention, the device further comprises a padded elastic cover around at least a portion of the ring.

In an embodiment of the invention, the device further comprises a removal string configured to detach a distal end of the connection block from the ring upon the application of a proximal force on the removal string.

There is further provided in accordance with an exemplary embodiment of the invention, a device sized and shaped for alleviating organ prolapse when inserted into a vagina, comprising: (a) an adjustably flexible, substantially planar ring; (b) a lower tube configured with a plurality of snapping elements at a distal end of the tube; (c) an upper tube configured with slots through which the snapping elements are removably inserted in order to releasably lock the lower and upper tubes and to place the device into a collapsed state, where the lower tube is coaxial with and internal to the upper tube; and, (d) a central post configured to be coaxially slidable within the lower tube to unlock the snapping elements from the slots to transition the device into an expanded state.

In an embodiment of the invention, the device further comprises a detachable connection block provided to a distal end of the upper tube and configured to attach to the ring.

In an embodiment of the invention, the device further comprises a removal string attached to the detachable connection block.

In an embodiment of the invention, the device further comprises a padded elastic cover around at least a portion of the ring.

There is further provided in accordance with an exemplary embodiment of the invention, a device sized and shaped for alleviating organ prolapse when inserted into a vagina, comprising: (a) an adjustably flexible, substantially planar ring; (b) an upper telescopic element connecting to the ring; (c) a lower telescopic element, coaxial with, internal to and slidable relative to the upper telescopic element, connected to the ring opposite the upper telescopic element; and, (d) an extension spring interconnecting the upper telescopic element to the lower telescopic element, where contraction of the extension spring is configured to transform and lock the device into an expanded state.

In an embodiment of the invention, a distal end of the extension spring is attached to a detachable spring holder.

In an embodiment of the invention, the spring holder is located in a distal end of the lower telescopic element.

In an embodiment of the invention, the device further comprises a string operatively connected to a proximal end of the spring holder.

In an embodiment of the invention, the device further comprises at least one protruding element located in a corresponding groove where the element is configured to deform the spring holder when the string is pulled, disconnecting the spring connection between the lower telescopic element and the upper telescopic element for transition of the device to a collapsed state.

In an embodiment of the invention, the device further comprises a padded elastic cover around at least a portion of the ring.

In an embodiment of the invention, the device further comprises an applicator configured to insert into and deploy the device in a vagina, comprising, (a) a holder configured to hold the device in a compressed state, and, (b) a plunger configured to move axially within the holder and to transition the device being held in the holder from the compressed state into the expanded state.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example, and not necessarily to scale, and are for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

The present invention, in some embodiments thereof, relates to the health care industry and, more particularly, but not exclusively, to devices and methods for treating feminine pelvic organ prolapse.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways. It should also be understood that in this specification, "distal" or "distally" means in the direction of or on the side of the cervix and "proximal" or "proximally" means in the direction of or on the side of the vaginal introitus. In this application, the "second" end or side corresponds to the distal side and the "first" end or side corresponds to the proximal side of the device and/or applicator.

The Devices Generally

In general, devices and methods are described for the treatment of feminine pelvic organ prolapse. It should be understood that features, forms and/or functions overlap among some or many of the embodiments that will be described herein and that description in relation to one embodiment may also apply to others. For brevity and efficiency, many of these common features and/or forms and/or functions are described only in this "Generally" section but apply to one, some or all embodiments. Specific distinctions between embodiments in features, form and/or function are described in additional sections below.

In some embodiments of the invention, the devices described herein are generally planar (extend substantially in 2 dimensions) and exhibit a stable, un-forced and/or naturally open, expanded state and are reversibly transitionable to a collapsed state. In some embodiments of the invention, the device is substantially ring or circular shaped, although the device could also be rhomboid, ovoid, drop-shaped, multi-sided (hexagonal, pentagonal, octagonal, etc.), as examples. Different exemplary device embodiments are described in detail below.

The device, or at least the ring portion of the device, is constructed of a bio-compatible material or materials and, optionally, of a material or materials which do not facilitate vaginal flora changes. Exemplary materials include high density polyurethane (for the plastic/skeletal part) and thermoplastic elastomers or silicone for the cover. In some embodiments of the invention, the device is configured to be permeable or to allow vaginal secretions to exit the vagina.

In some embodiments of the invention, the external surface of the device is smooth, for example to increase comfort to the user, reduced accumulated discharge and/or reduce the production of biofilms.

In an embodiment of the invention, the ring is at least partially covered by a padding or exterior layer (which would then be the external surface of the device, taking the place of the ring itself as the external surface). Optionally, the layer is configured to at least enhance user comfort and/or to reduce or prevent tissue necrosis. Optionally, the layer is configured to permit vaginal secretions to exit the vagina. In an embodiment of the invention, the layer is elastic. Optionally, the layer is rigid.

In some embodiments of the invention, a removal string is operatively connected to the device to enable a user to displace the device from the vagina and remove it from her body.

In an embodiment of the invention, a locking mechanism is provided to the device, for example to enable the device to lock into an expanded and/or closed state.

In some embodiments of the invention, the device is bi-stable. Optionally the bi-stable feature is facilitated by the locking mechanism. In some embodiments of the invention, the locking mechanism is activated by an applicator used for inserting the device. In some embodiments of the invention, the normally expanded device is temporarily held in a collapsed, storage state by the applicator. Different exemplary applicator embodiments are described below, at least with respect to FIGS. 4A-B. In some embodiments of the invention, the locking mechanism is deactivated by the removal string. In some embodiments of the invention, the locking mechanism is activated and/or deactivated by something other than mechanical forces, for example using magnetic, electric, pneumatic, and/or hydraulic force.

The devices described herein are configured to accommodate a plurality of vaginal sizes and/or shapes, in some embodiments of the invention. For example, the devices optionally are provided in a variety of sizes and/or shapes and/or flexibilities.

In some embodiments of the invention, determination of which specific device is most appropriate for a certain user is performed by a sizing device configured for indicating a device size to the user or to an attending medical professional. In some embodiments of the invention, the sizing device changes diameter and/or configuration to known device sizes and/or configurations in order to determine the proper device that should be used by the user. In some embodiments of the invention, a "fit-kit", comprised of a plurality of different sized devices (or dummies representing different device sizes), is used by the physician, or by the patient to self-diagnose, to find the proper size by trying out the different sizes until the most appropriate one is found. In some embodiments of the invention, an attending medical professional uses the fit-kit. In some embodiments of the invention, the devices are provided in a set of specific sizes, for example 61-67-73-79-85-91 mm, where the sizes vary by a set amount (e.g. 6 mm). However, in some embodiments of the invention, the device sizes vary by different amounts between sizes, for example the sizes may vary by 3-10 mm between different sizes.

In some embodiments of the invention, device shape is predefined but not permanent, that is, once deployed inside the patient the flexibility of the device allows some shape matching to the user's individual anatomical features. In some embodiments of the invention, the device exhibits an expanded diameter of 55-97 mm, depending on the embodiment. In some embodiments of the invention, the devices exhibit collapsed or compacted diameters of 20-40 mm. In some embodiments of the invention, the device does not exhibit a uniform flexibility around the circumference of the ring. For example, the ring is rigid at 0° and 180° (points corresponding to the axis of the locking mechanism or the axis of insertion using an applicator) but is flexible at all other points. As another example, the ring is rigid at 0° and 180°, is less rigid at 90° and 270° and is flexible elsewhere. In some embodiments of the invention, the ring increases in rigidity towards 0° and 180° and increases in flexibility towards 90° and 270°. In some embodiments of the invention, the ring is configured such that mirror image portions of the ring (any subsection up to and between 180°) flex towards each other, for example at 45 and 135 degrees and/or at the exact opposite. In some embodiments of the invention, the ring exhibits alternating, regular rigidity and/or flexibility around the circumference of the ring. In some embodiments of the invention, flexibility of the ring corresponds to planes of flexibility.

It should be understood that these are examples only, and that any combination of rigidity and flexibility, including no rigidity or no flexibility are permitted, depending on the intended use and/or needs of the user.

In some embodiments of the invention, sizes and/or shapes and/or flexibilities are chosen to reduce pressure on vaginal walls and/or provide better force distribution of the device on vaginal walls and/or to reduce the probability of pressure necrosis, optionally in combination with the padded cover/exterior layer.

In some embodiments of the invention, the device and the applicator, together, comprise a system for inserting and deploying the prolapse alleviating device.

In some embodiments of the invention, the device and/or the applicator is disposed of after use. In some embodiments of the invention, the device is reusable and/or configured to be reused (for example, is washable/sterilizable). In some embodiments of the invention, at least a component of the applicator is reusable, for example a holder element and/or a pushing element.

Function and Modes of Operation

In some embodiments of the invention, operation of the devices described herein can be divided into three general phases: i.) insertion, ii.) use (i.e. wearing the device), and iii.) removal.

With respect to insertion, devices are inserted with a particular predetermined orientation (or with orientation assistance) or are not sensitive to insertion orientation, depending on the particular embodiment. In some embodiments of the invention, devices described herein are inserted in a closed, compacted and/or collapsed state for ease of storage and/or insertion.

In some embodiments of the invention, devices are inserted manually, without an applicator. Optionally, the user or a caregiver inserts the device manually.

In some embodiments of the invention, devices are inserted with an applicator, which optionally also assists with orientation. In some embodiments of the invention, depth of insertion is a factor to be considered. Optionally, an applicator used for inserting a device is configured, for example the grip of the applicator is located such that proper insertion depth is established when the patient inserts the device until the fingers holding the applicator touch the labia. In some embodiments of the invention, the applicator is disposed of after device insertion and/or deployment.

In some embodiments of the invention, at least one of the devices (optionally including an applicator) described herein is configured to be inserted and/or deployed with only one hand. In other cases the applicator may be held with two hands (fingers 1+3 of both hands, and the plunger pushed forward with the 2 index fingers, or held with two hands and plunger pushed with one index finger. In some embodiments of the invention, at least one device (optionally including an applicator) is configured to be insertable and/or deployable regardless of the user's position, for example while the user is in a supine, standing or sitting position. In some embodiments of the invention, at least one device (optionally including an applicator) is configured to be insertable and/or deployable minimizing user self-touching. For example, the user does not have to separate the labia in order to insert the device and/or does not need to insert fingers into the vagina in order to position the device.

In some embodiments of the invention, the device is configured to properly position and/or orient itself into treatment rendering position during and/or after insertion. For example, the device is designed so that if the user inserts the device as instructed, with both parts of the applicator facing anteriorly and posteriorly, the device will always position itself bilaterally within the vagina. In addition, vaginal muscles will turn the device to the correct position, even if unintentionally it was inserted the wrong way.

With respect to usage of the devices described herein, in some embodiments of the invention they are inserted into the user in order to treat pelvic organ prolapse and/or to support the vaginal walls, that is, to provide support from the vagina against organs sagging down into the vaginal canal. In some embodiments of the invention, devices described herein are expanded and/or change state for use. In some embodiments of the invention, the devices described herein treat pelvic organ prolapse by stretching vaginal walls, optionally laterally, flattening the anterior and posterior vaginal walls and thereby reducing anterior and posterior prolapse. In some embodiments of the invention, any structure in the center of the ring of a device also passively assists the treatment of prolapse by inhibiting further decent into and through the center of the ring, for example a combination of telescoping tubes and/or a central post or rod. In some embodiments of the invention, a space occupying characteristic of the devices described herein treat apical prolapse, whereby the vaginal apex (uterine/vault) is not allowed to descend. The devices described herein are removed after insertion periodically. Optionally, the devices herein are reusable.

In some embodiments of the invention, the devices described herein are configured to elute pharmaceutical substances into the user.

With respect to removal of the devices described herein, the devices change from an expanded and/or deployed state into a closed, compacted and/or collapsed state for ease of removal. Optionally the removal state/configuration is the same as the storage/insertion state/configuration. In some embodiments of the invention, removal is effectuated by pulling on a removal string which is operatively connected to the device. Optionally, forces applied to the removal string are configured to also cause state/configuration change of the device from an expanded state to a collapsed state. Optionally, in cases where vaginal walls are lax, a pull of the string will cause extraction of the device still in its deployed state, somewhat deformed due to its flexibility, before the pulling force on the locking mechanism comes into action. This depends on the resistance of the vaginal introitus, and when absent—the device may be removed painlessly and/or without collapse.

Exemplary Device Embodiments

Figure 1A:
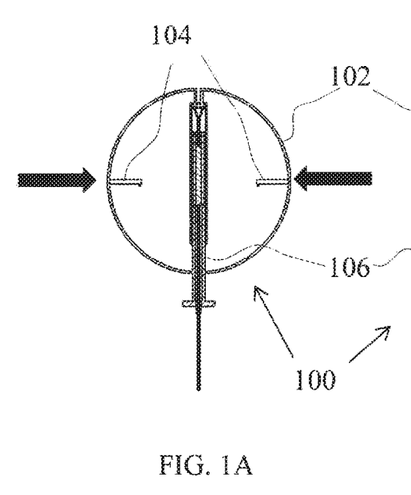
FIGS. 1A-C show side views of a prolapse treating device with snapping elements which snap into a central post, in accordance with an exemplary embodiment of the invention.
Figures 1B, 1C:
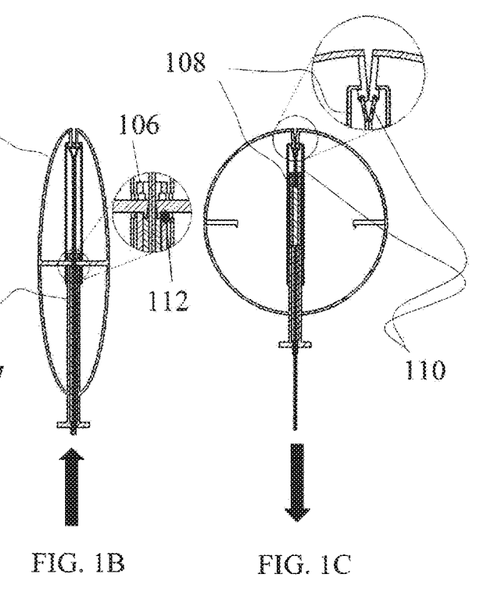

Referring to FIGS. 1A-C, a device 100 for supporting a prolapsed organ is shown, in accordance with an exemplary embodiment of the invention. Device 100 is configured with a body 102 capable of transforming between two states: a stick-like, collapsed state (shown in FIG. 1B) that enables easy storage and/or insertion and/or removal of the device into/from a vagina, and ring-like, expanded state to allow support of prolapsed organ from within the vagina.

In an embodiment of the invention, the device 100 is configured to naturally retain the expanded state, shown in FIGS. 1A and 1C.

In an embodiment of the invention, the body comprises at least two arcs to form the ring shape. Snapping elements 104 are provided to each of the arcs (for example, at 3 and 9 o'clock of the device) that are attachable to slots 112 within a central rod 106, in an embodiment of the invention. Prior to insertion of the device 100 into the vagina the user presses the device arcs (for example, at 3 and 9 o'clock) inward until the snapping elements 104 snap into slots 112 in the central rod 106 (preventing the arcs from returning to the expanded state) and thus transfers the device 100 to the stick like state. After insertion of the device 100 into the vagina, the user pushes (or pulls) the central rod 106 to release the snapping elements 104 (releases the arches) converting the device into the natural expanded state.

In an embodiment of the invention, the arcs are connected at their upper, distal side (and/or lower, proximal side) to a detachable connection block 108. In an embodiment of the invention, the connection block 108 is co-axially slidable over the central rod 106 and is also provided with slots which align with the slots 112 of the central rod 106 for passage of the snapping elements 104 therethrough when the device 100 is in the collapsed state. A removal string 110 is connected to the connection block 108, in an embodiment of the invention. By pulling the string 110, the connection block 108 is detached from both arcs, removing the force causing the arcs to flex, and thereby allowing the arcs to substantially straighten. The un-tensioned, collapsed structure of the device allows for an easy removal of it out of the vagina. A similar removal process is shown and described in more detail in FIG. 2C, with respect to a slightly different embodiment.

Figures 2A, 2B, 2C, 2D:
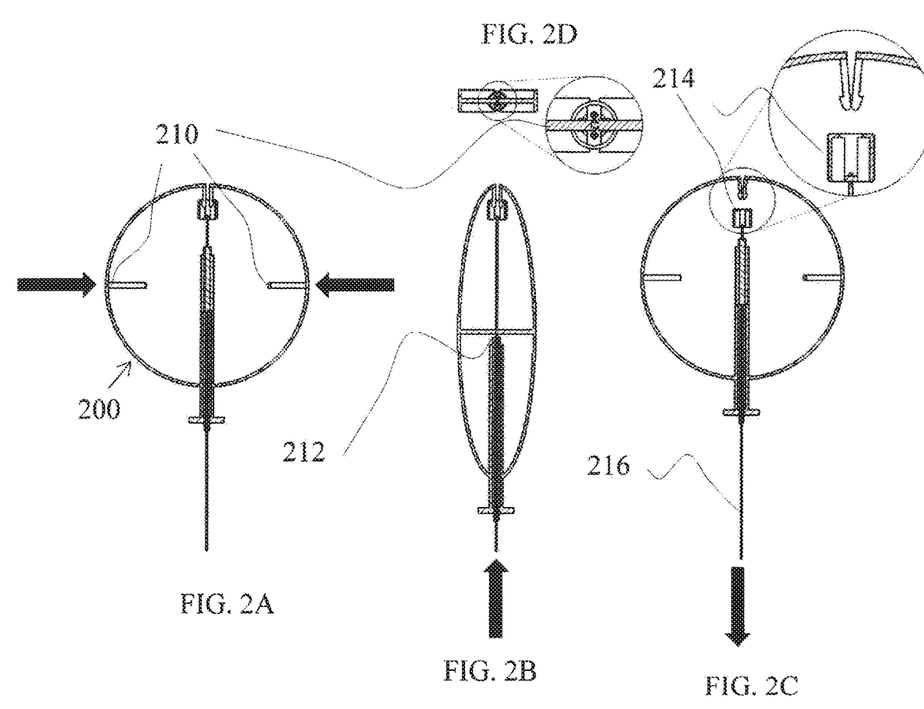
FIGS. 2A-C show side views of a prolapse treating device with self-snapping snapping elements, in accordance with an exemplary embodiment of the invention.
FIG. 2D is a top view of the device of FIGS. 2A-C, in accordance with an exemplary embodiment of the invention.
Figure 3A:
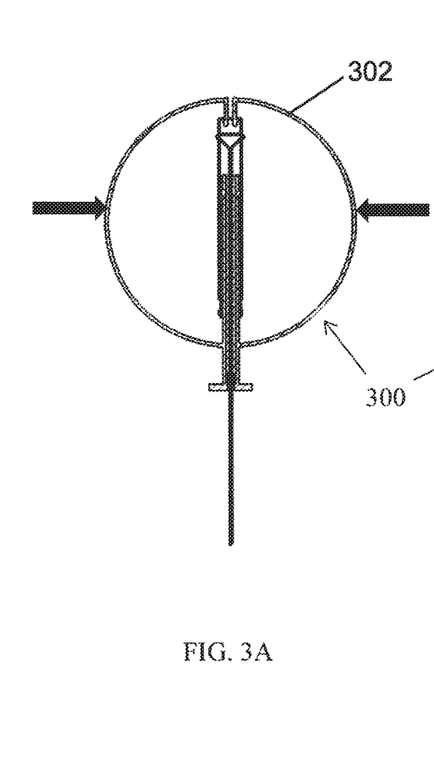
FIGS. 3A-D show side views of a prolapse treating device with a central post, in accordance with an exemplary embodiment of the invention.
Figure 3B:
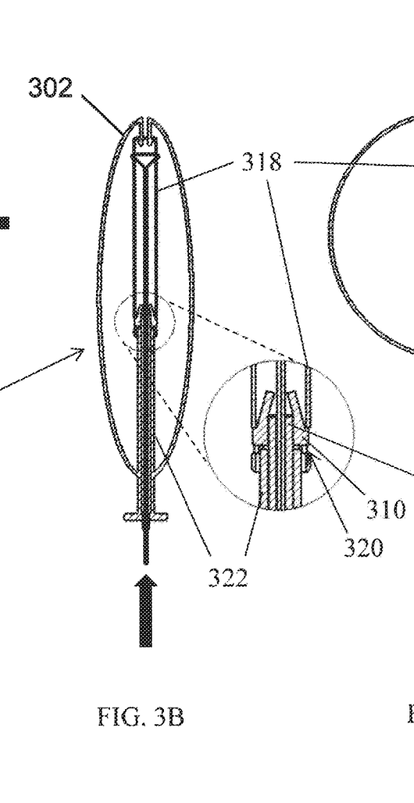
Figures 3C, 3D:
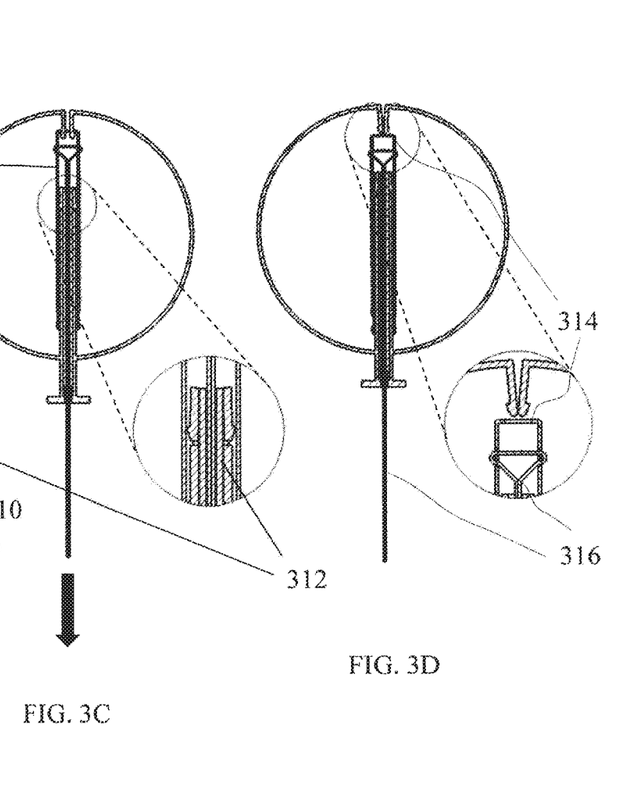

FIGS. 2A-C show side views of a prolapse treating device 200 with self-snapping elements 210, in accordance with an exemplary embodiment of the invention. As described elsewhere herein for other devices, device 200 is configured to have a naturally expanded, ring-like state for supporting prolapsed organs from within a vagina but is capable of transitioning to a collapsed state for storage, insertion and/or removal. In an embodiment of the invention, the body comprises at least two opposing arcs to form the ring shape. Similar to device 100, device 200 is provided with snapping elements 210, however, these elements 210 snap to each other rather than into slots. This arrangement can be seen in more detail in FIG. 2D, a top view of device 200.

In an embodiment of the invention, snapping elements 210 that are attachable to each other (which then connect the arcs to each other) are provided to each of the arcs (for example, at 3 and 9 o'clock of the device 200). Prior to insertion of the device into the vagina, the user presses the arcs (for example at 3 and 9 o'clock) inward until the self-snapping elements 210 snap to each other transferring the device 200 to a collapsed state and preventing the arcs from automatically returning the device to the steady state ring configuration) and thus transfer the device to the stick like configuration. After insertion of the device 200 into the vagina, the user pushes (or pulls) a central rod 212 on a central axis of the device 200 to release the snaps 210, releasing the device from the collapsed state, and transferring the device 200 back to the expanded, ring like state.

In an embodiment of the invention, the arcs are connected at their upper, distal side (and/or lower, proximal side) to a detachable connection block 214. A removal string 216 is connected to the connection block 214, in an embodiment of the invention. By pulling the string 216, the connection block 214 is detached from both arcs, removing the force causing the arcs to flex, and thereby allowing the arcs to substantially straighten. The un-tensioned, collapsed structure of the device allows for an easy removal of it out of the vagina.

FIGS. 3A-D show side views of a prolapse treating device 300 with a central post 312, in accordance with an exemplary embodiment of the invention. Device 300 is configured with a body 302 capable of transforming between two states: a stick-like, collapsed state (shown in FIG. 3B) that enables easy storage and/or insertion and/or removal of the device into/from a vagina, and ring-like, expanded state (shown in FIGS. 3A and 3C) to allow support of prolapsed organ from within the vagina. In an embodiment of the invention, the device 300 is configured to naturally retain the expanded state.

In an embodiment of the invention, the device 300 comprises telescoping sliding tubes. An upper tube 318 is provided with slots 320 through which snapping elements 310 are removably inserted in order to releasably lock the telescoping sliding tubes with respect to each other. In an embodiment of the invention, the snapping elements 310 are part of a lower tube 322 of the telescoping sliding tubes, where the lower tube 322 is coaxial with and internal to the upper tube 318. In an embodiment of the invention, the snapping elements 310 are located at a distal end of the lower tube 322.

In an embodiment of the invention, the body comprises at least two arcs to form the ring shape. Prior to insertion of the device 300 into the vagina the user presses the device arcs (for example, at 3 and 9 o'clock) inward until the snapping elements 310 snap into slots 320 of the upper tube 318 (preventing the arcs from returning to the expanded state) and thus transfers the device 300 to the collapsed state. After insertion of the device 300 into the vagina, the user pushes (or pulls) the central post 312 to release the snapping elements 310 (releases the arches) converting the device 300 back into the natural, expanded state.

In an embodiment of the invention, the arcs are connected at their upper, distal side (and/or lower, proximal side) to a detachable connection block 314. A removal string 316 is connected to the connection block 314, in an embodiment of the invention. By pulling the string 316, the connection block 314 is detached from both arcs, removing the force causing the arcs to flex, and thereby allowing the arcs to substantially straighten. The un-tensioned, collapsed structure of the device allows for an easy removal of it out of the vagina.

Figures 4A, 4B:
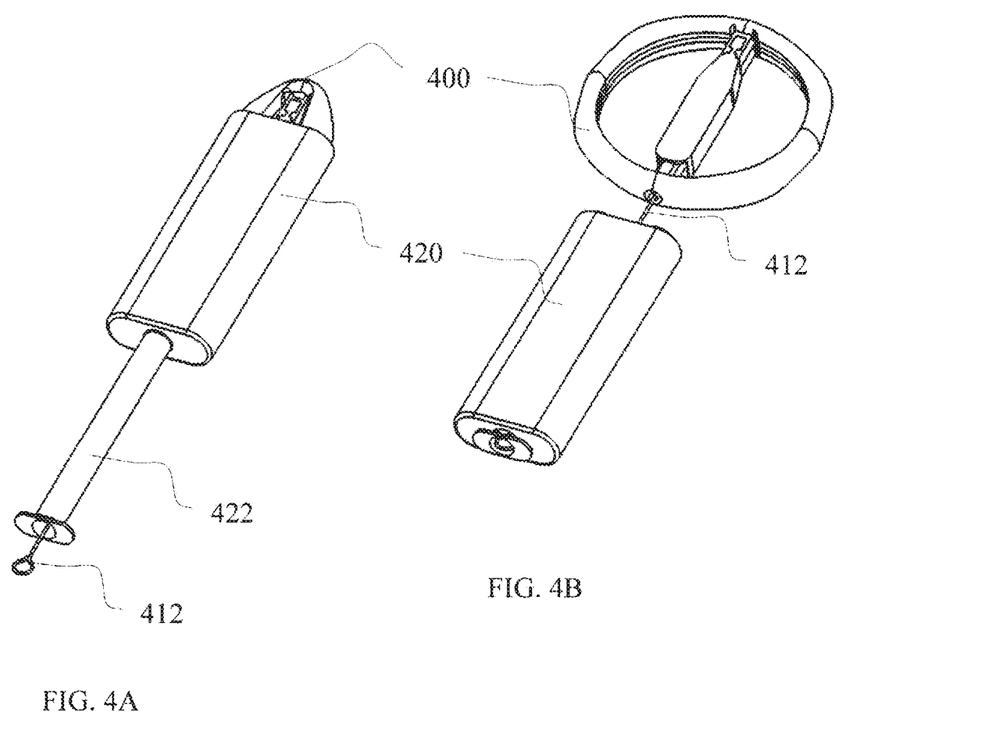
FIGS. 4A-B are perspective views of a device with an internal extension spring and an applicator, in accordance with an exemplary embodiment of the invention.

FIGS. 4A-B are perspective views of a device 400 with an internal extension spring 510 (shown in FIGS. 5A-C) and an applicator 420, in accordance with an exemplary embodiment of the invention. In an embodiment of the invention, the device 400 is pressed into a compressed state and inserted into a shaped applicator 420 shaped and configured to retain the device 400 in the compressed state. The applicator 420 has a co-axial plunger 422 configured to push the device 400 out of the applicator 420.

Figures 5A, 5B:
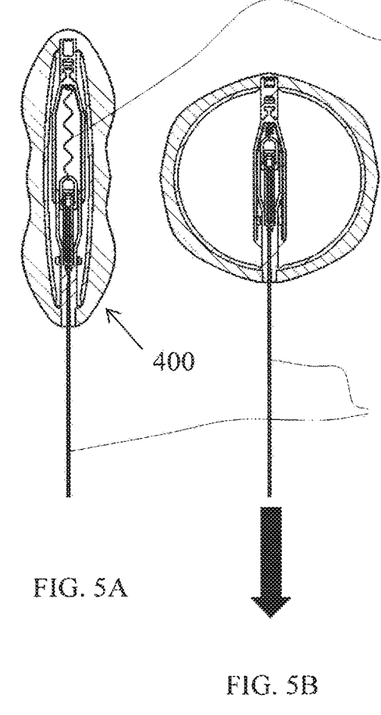
FIGS. 5A-C are cross-sectional views of the device shown in FIGS. 4A-B in various states of operation, in accordance with an exemplary embodiment of the invention.
Figure 5C:
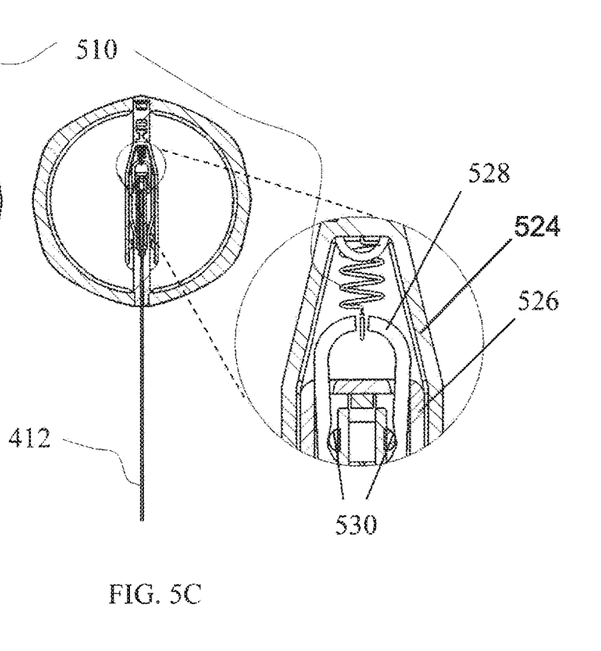

FIGS. 5A-C are cross-sectional views of the device 400, shown in FIGS. 4A-B, in various states of operation, in accordance with an exemplary embodiment of the invention. In an embodiment of the invention, once the device 400 is pushed out of the applicator 420, it expands into a ring like configuration (for example, shown in FIGS. 4B and 5B). In an embodiment of the invention, an extension spring 510 connects two telescopic elements. An upper telescopic element 524 is connected to the upper side of the device 400 while a lower telescopic element 526 is connected to the lower side of the device 400. The distal end of the spring 510 is attached to a detachable spring holder 528. The spring holder 528 is situated in distal end of the lower telescopic element 526. Contraction of the extension spring 510 transforms and locks the device 400 in the ring like configuration.

A string 412 is operatively connected to the proximal end of the spring holder 528, in an embodiment of the invention. The expanded detail of FIG. 5C shows the spring 510, spring holder 528 and two protruding elements 530 which are located in corresponding groves within the spring holder 528. By pulling the string 412, the spring holder 528 is deformed due to sliding against the protruding elements 530 creating a gap in its upper side, thus, disconnecting the spring 510. The spring disconnection frees the lower telescopic element 526 and allows it to move away from the upper telescopic element 524, returning the device 400 to a collapsed state for removal.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof. Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A device sized and shaped for alleviating organ prolapse when inserted into a vagina, comprising:
   (a) an adjustably flexible, substantially planar ring having an outer circumference and provided with two or more opposing snapping elements disposed on an inside surface of the outer circumference of the adjustably flexible, substantially planar ring and wherein the two or more opposing snapping elements extend towards each other;
   (b) a central rod extending at least partially through the adjustably flexible, substantially planar ring transverse to the snapping elements, where the central rod is provided with counterpart slots configured for insertion of the snapping elements therein; and
   (c) a connection block, co-axial with the central rod and slidable thereover to transition the device from an expanded state to a collapsed state, configured with slots which align with the counterpart slots of the central rod for passage of at least one snapping element therethrough when the device is in the collapsed state.

2. A device according to claim 1, where one opposing snapping element snaps to another opposing snapping element both of which pass through the counterpart slots of the central rod and the slots of the connection block.

3. A device according to claim 1, further comprising a padded elastic cover around at least a portion of the adjustably flexible, substantially planar ring.

4. A device according to claim 1, further comprising a removal string configured to detach a distal end of the connection block from the adjustably flexible, substantially planar ring upon the application of a proximal force on the removal string.

5. A device according to claim 1, where the two or more opposing snapping elements are configured to removably attach to each other to configure the device in a collapsed state and where the central rod is slidable to detach the self-snapping elements from each other to return the device to an expanded state.

6. A device according to claim 5, further comprising a padded elastic cover around at least a portion of the adjustably flexible, substantially planar ring.

7. A device according to claim 5, further comprising a removal string configured to detach a distal end of the connection block from the adjustably flexible, substantially planar ring upon the application of a proximal force on the removal string.

8. A device sized and shaped for alleviating organ prolapse when inserted into a vagina, comprising:
   (a) an adjustably flexible, substantially planar ring;
   (b) a lower tube configured with a plurality of snapping elements forming a tip of the lower tube at a distal end of the lower tube;
   (c) an upper tube configured with slots through which the plurality of snapping elements are removably inserted in order to releasably lock the lower and upper tubes and to place the device into a collapsed state, where the lower tube is coaxial with and internal to the upper tube; and
   (d) a central post configured to be coaxially slidable within the lower tube to unlock the plurality of snapping elements from the slots to transition the device into an expanded state.

9. A device according to claim 8, further comprising a detachable connection block provided to a distal end of the upper tube and configured to attach to the adjustably flexible, substantially planar ring.

10. A device according to claim 9, further comprising a removal string attached to the detachable connection block.

11. A device according to claim 8, further comprising a padded elastic cover around at least a portion of the adjustably flexible, substantially planar ring.

* * * * *